United States Patent [19]

McNabb

[11] Patent Number: 6,077,976
[45] Date of Patent: Jun. 20, 2000

[54] PROCESS FOR RECOVERY OF AMINOALCOHOLS FROM AQUEOUS SOLUTIONS CONTAINING INORGANIC SALTS

[75] Inventor: Andy J. McNabb, Lake Jackson, Tex.

[73] Assignee: BASF Corporation, Southfield, Mich.

[21] Appl. No.: 09/215,721

[22] Filed: Dec. 17, 1998

[51] Int. Cl.[7] .................................................. C07C 209/00
[52] U.S. Cl. .............................................................. 564/497
[58] Field of Search ...................................... 564/497, 498

[56] References Cited

U.S. PATENT DOCUMENTS

| | | | |
|---|---|---|---|
| 3,966,594 | 6/1976 | Ohkawa et al. | 210/22 |
| 4,487,698 | 12/1984 | Idel et al. | 210/639 |
| 4,518,502 | 5/1985 | Burns et al. | 210/634 |
| 4,818,410 | 4/1989 | Bellos et al. | 210/639 |
| 4,839,054 | 6/1989 | Ruebush et al. | 210/639 |
| 4,948,511 | 8/1990 | Swanson et al. | 210/634 |
| 5,364,532 | 11/1994 | Bellos et al. | 210/639 |
| 5,705,074 | 1/1998 | Brient | 210/634 |

FOREIGN PATENT DOCUMENTS 0 586 107 A1  3/1994  European Pat. Off. .......... C02F 1/26

*Primary Examiner*—Samuel Barts

[57] ABSTRACT

A process for recovery of aminoalcohols from aqueous solutions containing inorganic salts is disclosed. The aqueous solution which contains aminoalcohols is then mixed with a base in order to increase the ph and the solution is then extracted with an alkyphenol solvent.

7 Claims, No Drawings

PROCESS FOR RECOVERY OF AMINOALCOHOLS FROM AQUEOUS SOLUTIONS CONTAINING INORGANIC SALTS

The present invention is directed to a process for the recovery of aminoalcohols from aqueous streams containing inorganic salts. The present invention is related to co-pending application Ser. No. 09/215,399 filed Dec. 18, 1998 which is incorporated herein by reference.

BACKGROUND OF THE INVENTION

A variety of industrial processes generate aqueous waste steams containing contaminating amounts of organic compounds. Before such streams can be discharged into a receiving body of water, the organics content must be substantially reduced to meet state and federal regulatory standards.

For example in the manufacture of polyethyleneimine the process usually generates water waste streams. The water may contain significant amounts of dissolved sodium salts and other contaminating hydrocarbons. A problem is that it contains aminoalcohols. If not removed, these contaminants are measured as oil and grease when the water is acidified and freon extracted, pursuant to EPA gravimetric test methods. Thus, it is desirable to treat such waster so that it can be discharged without violating regulatory standards.

Previous workers in the field attempted to remove dissolved organic contaminants by acidification. They believed that the dissolved organics would form a free oil phase at low pH" and could be removed by settling or flotation. For example, U.S. Pat. No. 4,401,570 discloses a method of removing organic esters from waste water using acidification. We have found, however, that these organics are too finely dispersed to allow them to settle or float. Thus, the organics remained and continued to result in unacceptable levels of oil and grease in the water stream.

Accordingly, it is the principle object of this invention to economically remove water-soluble organics from waste streams.

SUMMARY OF THE INVENTION

This invention concerns a process for removing aminoalcohols from waste streams. The process comprises: forming a mixture, agitating the mixture to produce a thoroughly mixed phase; and separating the phase to produce a free oil phase and a clean water phase.

The aqueous stream containing aminoalcohols and organic salts is mixed with a base (such as sodium hydroxide or potassium hydroxide) in order to increase the pH of the wastewater to a pH of 9–13.5. The aqueous stream is then extracted with an alkylphenol solvent (such as Butylphenol, Octylphenol, Nonylphenol, Dodecylphenol). The extract contains the solvent and much of the TOC originally present in the aqueous stream. The raffinate contains the aqueous salt solution. The solvent is recycled in order to minimize operating costs. An inorganic acid (such as sulfuric acid or hydrochloric acid) is added to the raffinate for neutralization. The raffinate (the aqueous stream) can then be treated at much lower costs in a biological treatment plant and/or activated carbon system.

The extract is sent to a distillation system. Light impurities are removed in the overheads in the first distillation tower and the aminoalcohol is recovered as a side stream product. The bottom stream contains the solvent and other impurities and is the feed to a second distillation tower. Intermediates are removed in the overheads of the second tower, the solvent is removed as a sidestream product and recycled, and heavy impurities are removed in the distillation residue. The light, intermediate, and heavy impurities can be either incinerated for fuel value, sold as by-products, or used for other applications.

EXAMPLE 1

For Recovery of Aminoalcohols

The TOC of wastewater produced during the manufacturing of Polyethyleneimine was measured and found to be 6500 ppm. The sodium sulfate content of the wastewater was approximately 20%. Caustic was added to the wastewater until a pH of 11 was obtained. The wastewater was extracted one time with Butylphenol at 90° C. using a solvent to feed ratio of 1:1. The TOC of the raffinate was measured and found to be 1,020 ppm, a TOC reduction of 84%. The extract contains Monoethanolamine, Butylphenol solvent, and other impurities. Since Monoethanolamine has a boiling point of 170° C. at 760 mm Hg and Butylphenol has a boiling point of 224° C. at 760 mm Hg, there is sufficient difference in boiling points to recover the monoethanolamine by conventional distillation techniques.

EXAMPLE 2

For Recovery of Aminoalcohols

The TOC of wastewater produced during the manufacturing of Polyethyleneimine was measured and found to be 6500 ppm. The sodium sulfate content of the wastewater was approximately 20%. Caustic was added to the wastewater until a pH of 13 was obtained. The wastewater was extracted three times with Octylphenol at 90° C. using a solvent to feed ratio of 2:1. The TOC of the raffinate was measured and found be 470 ppm, a TOC reduction of 92.5%. The extract contains Monoethanolamine, Butylphenol solvent, and other impurities. Since Monoethanolamine has a boiling point of 170° C. at 760 mm Hg and Octylphenol has a boiling point of 175° C. at 30 mm Hg, there is sufficient difference in boiling points to recover the Monoethanolamine by distillation.

I claim:

1. A process for recovery of aminoalcohols from an aqueous waste stream containing inorganic salts comprising forming a mixture of the aqueous stream and a base, agitating the mixture to produce a thoroughly mixed phase, separating the mixed phase by extraction to produce a free oil phase and a clean water phase, adding an inorganic acid to the clean water phase, and distilling the free oil phase.

2. The process of claim 1 wherein the waste stream is the by-product in the manufacture of polyethylenimine.

3. The process of claim 1, wherein the aqueous stream comprises aminoalcohols and organic salts.

4. The process of claim 1, wherein the base is sodium hydroxide or potassium hydroxide.

5. The process of claim 1, wherein the step of separating the mixed phase by extraction comprises extracting the aqueous stream with an alkylphenol solvent.

6. The process of claim 5, wherein the alkylphenol solvent is butylphenol, octylphenol, nonylphenol, or dodecylphenol.

7. The process of claim 1, wherein the inorganic acid is sulfuric acid or hydrochloric acid.

* * * * *